United States Patent
Master et al.

(10) Patent No.: US 11,232,856 B2
(45) Date of Patent: Jan. 25, 2022

(54) METHODS FOR AUTOMATIC COHORT SELECTION IN EPIDEMIOLOGIC STUDIES AND CLINICAL TRIALS

(71) Applicant: Engooden Health Inc., Framingham, MA (US)

(72) Inventors: Neel Master, San Francisco, CA (US); Peeyush Kumar, San Francisco, CA (US)

(73) Assignee: Engooden Health Inc., Framingham, MA (US)

( * ) Notice: Subject to any disclaimer, the term of this patent is extended or adjusted under 35 U.S.C. 154(b) by 69 days.

(21) Appl. No.: 16/458,592

(22) Filed: Jul. 1, 2019

(65) Prior Publication Data

US 2020/0075139 A1 Mar. 5, 2020

Related U.S. Application Data

(60) Provisional application No. 62/692,552, filed on Jun. 29, 2018.

(51) Int. Cl.
| | |
|---|---|
| *G16H 10/60* | (2018.01) |
| *G06F 16/21* | (2019.01) |
| *G16H 15/00* | (2018.01) |
| *G16H 10/20* | (2018.01) |
| *G06N 20/00* | (2019.01) |
| *G06F 40/30* | (2020.01) |

(52) U.S. Cl.
CPC ............ *G16H 10/60* (2018.01); *G06F 16/212* (2019.01); *G06F 40/30* (2020.01); *G06N 20/00* (2019.01); *G16H 10/20* (2018.01); *G16H 15/00* (2018.01)

(58) Field of Classification Search
CPC ........ G16H 10/20; G16H 10/60; G16H 50/20; G16H 50/70; G16H 15/00; G16H 30/40; G16H 50/30; G16H 20/10; G16H 20/40; G16H 40/67; G16H 50/50; G16H 70/60; G16H 10/40
See application file for complete search history.

(56) References Cited

U.S. PATENT DOCUMENTS

| | | | | |
|---|---|---|---|---|
| 2018/0046780 A1* | 2/2018 | Graiver | ................. | G06F 40/205 |
| 2020/0005906 A1* | 1/2020 | Wang | .................... | G16H 10/60 |

* cited by examiner

*Primary Examiner* — Maroun P Kanaan
(74) *Attorney, Agent, or Firm* — Choate, Hall & Stewart; William R. Haulbrook; Samuel R. Polio

(57) ABSTRACT

Generally, the method provides an interface for clinical research organizations to estimate, in real-time, an eligible patient population for a clinical study, as well as a point-of-care interface that can alert patients of their eligibility in a clinical study. Thus, the method provides improved identification of clinical cohorts and can quickly match patients with clinical studies that fit their medical needs.

10 Claims, 2 Drawing Sheets

Patient Queue

Cohort

Sophia Mann
RN

- (N) Eligible not enrolled
- (P) Pending enrollment ▼
- (C) Currently Enrolled ▼
- (I) Ineligible
- (D) Declined ▼
- (X) Dis-enrolled Inclusion criteria: problems: "diabetes type 2" + medications: "metformin"
+ vitals: "bmi≥27" + vitals: "bmi≤40"
Exclusion criteria: problems: "pregnant" + problems: "diabetes type 1" + problems: "CHF"

[SEARCH] Advanced Search

| SELECT | NAME | GENDER | DATE OF BIRTH | |
|---|---|---|---|---|
| | | | | ENROLL PATIENTS |
| ● (N) | Jeanette Campbell | F | 03/11/1976 | |
| ● (N) | Garrett McGuire | M | 06/09/1983 | |
| ● (N) | Grace Waters | F | 06/29/1991 | |

A/R Management  Chart

Patient Charts  Monday, April 27, 1
Hall, Amy (10

Facesheet  Summ

Visit: 4/20/2009

Patient Detected
Trial: Injecting Botulinum Toxin A Underneath the Skin to Treat Spinal Cord Pain in Patients With Spinal Cord Injury
NCT02736890

| Inclusion Criteria (DETECTED) | Exclusion Criteria (NOT DETECTED) |
|---|---|
| Ages between 18 and 80 ▼ | Pregnancy ▼ |
| Diagnosed with traumatic spinal cord injury ▼ | History of intolerance, hypersensitivity or known allergy to botulinum toxin or its preservatives ▼ |
| Target pain is considered by the physician as at level SCI in nature to a high degree of certainty (4 or 5) ▼ | History of intolerance, hypersensitivity or known allergy to EMLA cream ▼ |
| Target pain continuously present for at least one month ▼ | Recent history of administration of botulinum toxin (within previous 6 months) ▼ |

Patient enrollment date  06/7/2017

| | Confirmed | Physicians Initial | |
|---|---|---|---|
| 1. Does the patient acknowledge the warnings and risks of the clinical trial | ☑ | JB | ENROLL |
| 2. Does the patient understand that they may stop trial at any time | ☑ | JB | CANCEL |
| 3. Auto-generate enrollment form | ☑ | JB | |

*FIG. 3*

METHODS FOR AUTOMATIC COHORT SELECTION IN EPIDEMIOLOGIC STUDIES AND CLINICAL TRIALS

CROSS-REFERENCE TO RELATED APPLICATIONS

This application claims the benefit of U.S. Provisional Application No. 62/692,552, filed on 29 Jun. 2018, which is incorporated in its entirety by this reference.

TECHNICAL FIELD

This invention relates generally to the field of healthcare data processing and electronic health records and more specifically to a new and useful method for selecting a cohort for a clinical study in the field of healthcare data processing.

BRIEF DESCRIPTION OF THE FIGURES

FIG. 2 is a graphical representation of a first graphical user interface; and

FIG. 3 is a graphical representation of a second graphical user interface.

DESCRIPTION OF THE EMBODIMENTS

Figure 1:
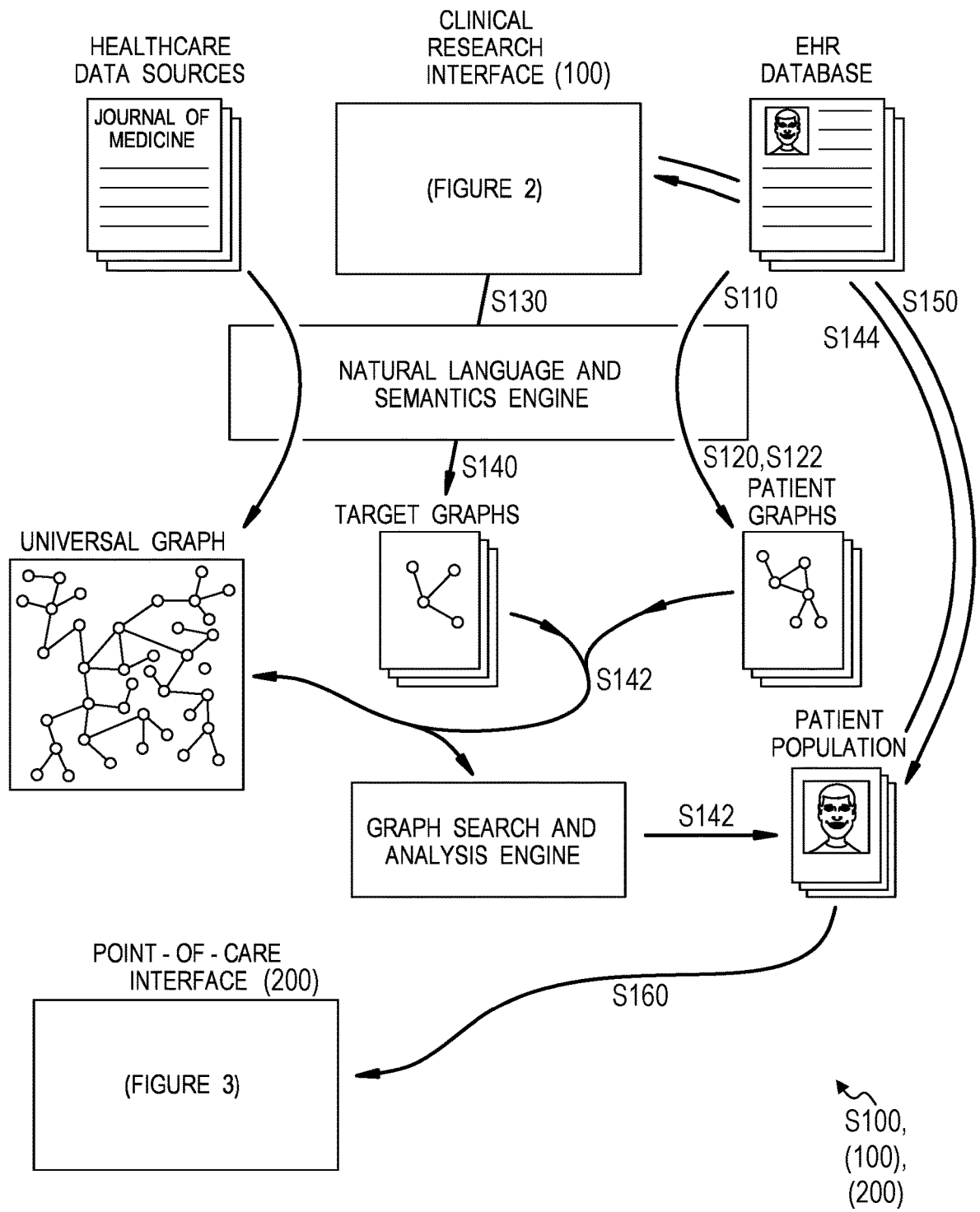
FIG. 1 is a flowchart representation of a method.

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

As shown in FIG. 1, a method for selecting a cohort for a clinical study, including: accessing from an electronic health record database, an unstructured electronic health record for each patient in a population of patients in Block S110; for each patient in the population of patients: transforming the associated unstructured electronic health records of the patient into a patient graph, the patient graph representing a set of clinical concepts and corresponding semantic roles for the patient in Block S120; and appending the patient graph to a set of patient graphs in Block S122; at a clinical research interface 100, recording a first set of inclusion and exclusion criteria in Block S130; transforming the first set of inclusion and exclusion criteria into a first target graph representing a first set of target clinical concepts for a clinical trial in Block S140; for each patient in the population of patients, in response to alignment between the patent graph of the patient and the first target graph, appending the patient to a first subpopulation of patients in Block S142; rendering a first representation of the first subpopulation of patients within the clinical research interface 100 in Block S144; at the clinical research interface 100, recording a second set of inclusion and exclusion criteria in Block S130; transforming the first set of inclusion and exclusion criteria and the second set of inclusion and exclusion criteria into a second target graph for the clinical trial in Block S140; for each patient in the population of patients, in response to alignment between the patient graph of the patient and the second target graph, appending the patient to a second subpopulation of patients in Block S142; rendering a second representation of the second subpopulation of patients within the clinical research interface 100 in Block S144; recording a selection of a potential clinical cohort from the second subpopulation of patients in Block S150; and, in response to access of a particular electronic health record of a particular patient included in the potential clinical cohort at a point-of-care interface 200, rendering an indication of the particular patient's eligibility for the clinical trial in Block S160.

2. Applications

Generally, the method S100 provides an interface for clinical research organizations (hereinafter "CRO"s) to estimate, in real-time, an eligible patient population for a clinical study, as well as a point-of-care interface 200 that can alert patients of their eligibility in a clinical study. Thus, the method S100 provides improved identification of clinical cohorts and can quickly match patients with clinical studies that fit their medical needs.

The method S100 is executed by a computer system connected to a set of medical data sources, an electronic health record database (hereinafter "EHR database"), a universal graph, a patient graph database, a clinical research interface 100, and a point-of-care interface 200 via the internet or a similar computer network. The computer system can include one or more servers executing code to perform the method S100.

In particular, the computer system uses natural language and semantics processing (hereinafter "NLP") to ingest a corpus of medical data to curate a universal graph. The computer system then leverages the universal graph to process electronic health records (hereinafter "EHR") of a population of patients in order to evaluate the eligibility of those patients for epidemiologic studies or clinical trials (hereinafter "clinical studies"). The computer system provides an interface for a CRO to establish inclusion and exclusion criteria for a potential clinical study. Upon establishment of inclusion and exclusion criteria, the computer system can identify a subpopulation of the patient population that may be eligible for the potential clinical study, based on the established criteria. By utilizing a graph search method, the computer system is capable of rendering real-time patient eligibility results and analysis as the computer system receives updated inclusion and exclusion criteria at the clinical research interface 100. The computer system can record a selection of a potential clinical cohort from the eligible population of patients and can then provide indications of each patient's eligibility for the clinical study at a point-of-care interface 200. The computer system can additionally record a patient's enrollment in the clinical study or declination of the clinical study at the point-of-care interface 200.

The computer system also provides improvement to the processing speed of medical data retrieval by leveraging the universal graph to perform an indexed search of patient profiles in near real-time. Typical searching techniques take a longer period of time to return results. Additionally, the computer system can provide more explanatory results by searching an explanatory clinical concept graph instead of a more basic searching technique.

3. Computer System

As shown in FIG. 1, the computer system includes computational components that execute the method S100. The computer system includes, a natural language and semantics engine, a universal graph database, and a graph search and analysis engine. Each of the computational components of the computer system execute subprocesses of the method S100. Depending on the implementation of method S100, different computational components can execute different subsets of the method S100. Additionally, the computer system is connected, via a network, to healthcare data sources, an EHR database, a patient graph database, one or more clinical research interfaces 100, and point-of-care interfaces 200. The computer system can communicate, via the network, to execute functions of a clinical research interface 100 and a point-of-care interface 200 on a computational device of a user, or the computer system can render the clinical research interface 100 and the point-of-care interface 200 on the server and serve it to a client device of the user.

3.1 Healthcare Data Sources

As shown in FIG. 1, the computer system utilizes healthcare data sources in order to generate a universal graph that provides conceptual and hierarchical context for the execution of the method S100. Generally, healthcare data sources are electronic documents stored in a variety of online locations. In one implementation, potential healthcare data sources can include: clinical concepts and ontologies, medical literature and research documents, medication labels, clinical guidelines and best practices, ICD-coded and anonymized EHR, and CPT-coded insurance claims data. The computer system typically accesses the healthcare data sources in an unstructured text, image, spreadsheet, or hybrid format, such as PDF. However, the computer system can process the healthcare data sources in any common format.

In one implementation, the computer system executes a natural language processing (or "NLP") and semantics engine to process the healthcare data sources and to generate a universal graph. In one variation, the computer system can generate multiple universal graphs, each of which can utilize different subsets of the healthcare data sources. For example, the computer system can generate a first universal graph based only on clinical concepts and ontologies and medical literature and research documents, and a second universal graph based on ICD-coded and anonymized EHR, and CPT-coded insurance claims data.

3.2 Natural Language Processing and Semantics Engine

As shown in FIG. 1, the NLP and semantics engine executes many of the steps of the method S100 and interfaces with all of the computational components of the computer system. The NLP and semantics engine performs a variety of functions required to convert unstructured medical data, such as in the form of electronic documents, to structured graph data, wherein nodes in the graph represent clinical concepts and wherein edges in the graph represent semantic roles corresponding to the clinical concepts. The NLP and semantics engine can perform this function on any of the aforementioned healthcare data sources, patient EHR, clinical research documents, and/or search terminology.

In one implementation, the NLP and semantics engine utilizes a pipeline flow to process the data source and output a graph structure or other representation of the clinical concepts in the data source. In one implementation, the NLP and semantics engine: detects clinical segments in the data source; identifies sentences in the detected clinical segments; tokenizes words from the identified sentences; annotates context dependent tokens (e.g. dates, lab values, codes, abbreviations); identifies the part of speech of each token; defines tokens based on a dictionary or clinical ontology; parses grammar using a dependency-constituency hybrid parser; associates semantic concepts to the outputs of the hybrid parser based on clinical guidelines and expert knowledge; filters semantic concepts based on context; expands the semantic concepts to include inferred relationships; and identifies uncertainties and negations. Once the NLP and semantics engine has processed input information, the NLP and semantics engine outputs a graph structure identifying clinical concepts from the input data as nodes and identifying semantic roles of the clinical concepts as edges. However, the computer system can implement any other NLP and semantics processing pipeline to output graphs or other representations of clinical contexts.

In one implementation, the NLP and semantics engine can output graph structures with nodes representing clinical concepts including anatomical sites, medications, lifestyle statuses, signs/symptoms, procedures, lab results, diseases/disorders, demographics, CPT and ICD codes, and/or clinical context, etc. The NLP and semantics engine can also output graph structures with edges representing semantic roles and relationships including grammatical relationships, temporal relationships, probabilistic equivocations (e.g. "probably," "significantly"), polarity/negation, conditionality (e.g. if/then relationships), history (e.g. patient history and family history), hierarchical relationships, inferred modifiers, and abbreviation/synonyms.

In one implementation, the computer system can improve the NLP and semantics engine using machine learning techniques. For example, the computer system can monitor the actions of a user in the clinical research interface 100 and utilize supervised learning algorithms based on the recorded actions of the user to refine the NLP and semantics engine.

3.3 Universal Graph Database

As shown in FIG. 1, the computer system includes a universal graph database. The universal graph database stores one or more universal graph structures that contain a curated set of clinical concepts and the semantic and hierarchical relationships between them. For example, a universal graph can contain a set of nodes representing human anatomy, wherein each node represents a more specific anatomical concept and is related hierarchically to more general concepts. In this example, a node representing the concept of organs in general relates to descendent nodes representing the heart, brain, stomach, liver, etc. each of which relates to additional descendent nodes describing more specific anatomical concepts such as the right atrium, right ventricle, left atrium, left ventricle, etc. for the heart alone.

The computer system can ingest a medical standard of clinical data or a large corpus of curated medical knowledge to generate the universal graph. Alternatively, the computer system can modify an automatically-generated universal graph based on expert feedback. In one implementation, the universal graph can include nodes indicating preferred terminology for clinical concepts as well as alternate names for the synonymous concepts.

In one implementation, the universal graph database can store multiple universal graphs for different concepts or functions of the computer system. For example, the computer system can generate a universal graph for an orthopedic context and another universal graph for a radiology context. It may be useful for the computer system to generate and store multiple universal graphs because some terms have different meanings across clinical contexts (e.g. SSRI can mean either Sliding Scale Regular Insulin or Selective-Serotonin Reuptake Inhibitor depending on context). The computer system can achieve similar disambiguation by generating universal graphs including nodes that represent various contexts. These nodes can be connected to other clinical concepts having the represented context.

3.4 EHR Database

As shown in FIG. 1, the computer system utilizes an EHR database to produce patient graphs in a process further described below. Generally, an EHR database can be a database utilized by any electronic health record keeping software (hereinafter "EHR software") at various points-of-care for a patient. Alternatively, the computer system maintains its own EHR database and aggregates EHR from multiple EHR software databases. Data stored in the EHR database is typically identified by patient, provider, and date of the particular record and, in some cases, can be categorized by department or facility. EHR data may also include summary data on a patient's vitals, medications, last visit to the provider, or any other information indicated by EHR software. However, EHR data can be unstructured and in the form of text, image, spreadsheet, or hybrid format, such as PDF. EHR data also include additional information on a patient's demographics, progress notes, problems, medications, vitals, past medical history, immunizations, laboratory data, radiology reports, and any other information that can be collected by a provider. In one example, EHR software includes the point-of-care interface 200, which can record EHR data to store it in the EHR database.

3.5 Graph Search and Analysis Engine

As shown in FIG. 1, the computer system includes a graph search and analysis engine. Generally, the graph search and analysis engine searches a set of patient graphs based on a target graph specified by the user at the clinical research interface 100 to determine similarity or exact matches between the target graph and the patient graphs or subgraphs of each patient graph and the target graph. More specifically, the graph search and analysis engine can perform a graph mining algorithm to determine whether the target graph is present as a subgraph of a patient graph or is similar to a subgraph of a patient graph. The computer system can display a patient's name associated with a patient graph, if the graph search and analysis engine identifies that the patient graph has a subgraph similar or identical to the target graph. For ease of explanation, a "match" between a target graph and a patient graph can refer to an exact match between a target graph and a subgraph of a patient graph or a sufficient similarity between a target graph and a subgraph of a patient graph. In one example, similarity between graphs can be calculated based on the number of shared nodes and edges, the number of structural differences between graphs, and the specific relationships identified in the edges.

In one implementation, the graph search and analysis engine identifies matching patient graphs in real time by indexing patient graphs within the universal graph. For example, for each patient graph, the graph search and analysis engine can identify the patient graph's representation in the universal graph by performing a graph mining algorithm. The patient corresponding to the patient graph can then be indexed at this location. The graph search and analysis engine can then perform the same process with a target graph and return all patients indexed at the representation of the target graph.

4. EHR Processing and Patient Graphs

As shown in FIG. 1, in Blocks S110 and S120 the computer system accesses, from an EHR database, an unstructured EHR for each patient in a population of patients; and for each patient in the population of patients: transforms the associated unstructured EHRs of the patient into a patient graph, wherein the patient graph represents a set of clinical concepts and corresponding semantic roles for the patient. Generally, the computer system accesses data from the EHR data and uses the NLP and semantics engine to create a patient graph for each patient based on the EHR data for that patient. The patient graph indicates the clinical concepts related to the EHR of the patient and the relationships between those concepts as semantic roles. In one example, the computer system can aggregate EHR data across multiple EHR databases created via different EHR software in order to generate a patient graph. After the computer system transforms the EHR data into a set of patient graphs, the patient graphs are then stored in the patient graph database for later processing. In one implementation, the computer system will periodically access the EHR databased in order to update the patient graphs with the latest patient EHR. Alternatively, the computer system can access additional EHR data in response to receiving an indication from the point-of-access interface that the EHR of a patient has been updated by a provider.

In one implementation, the computer system can periodically index the universal database by comparing the patient graphs to subgraphs of the universal graph. For example, as the computer system updates patient graphs in the patient graph database the computer system can perform graph mining algorithms to match the patient graphs with subgraphs of the universal graphs and create an index associated with the matching nodes and/or edges of the universal graph.

However, the computer system can represent patient data in any other way including non-graph database approaches.

5. Clinical Research Interface

As shown in FIG. 2, the computer system can render a clinical research interface 100 with which a user of the computer system can search for patients that satisfy the inclusion and exclusion criteria of a clinical study. The computer system can render the clinical research interface 100 on any computational device connected to the computer system through a network such as the internet. In one example, the clinical research interface 100 is rendered by a native application on a user's device associated with and in communication with the computer system. Alternatively, the clinical research interface 100 is rendered directly by the computer system and displayed on the user device via a web browser or native application.

The computer system interfaces with the user via the clinical research interface 100 to record inclusion and exclusion criteria in natural language. Alternatively, the computer system can upload a file of a clinical study selected by the user within the clinical research interface 100. The computer system can then implement NLP techniques to automatically extract inclusion and exclusion criteria from the natural language input or from the file. Once the computer system records inclusion and exclusion criteria, the computer system can generate a target graph representing the recorded inclusion and exclusion criteria. The computer system can then search the patient graphs to determine whether they match the target graph in order to identify patients that satisfy the inclusion and exclusion criteria. The aforementioned steps are discussed in more detail below.

5.1 Inclusion and Exclusion Criteria

As shown in FIG. 1, in Block S130 at a clinical research interface 100, the computer system records a first set of inclusion and exclusion criteria. Generally, inclusion and exclusion criteria are qualitative or quantitative criteria utilized for determining patient eligibility in a clinical study. Inclusion criteria specify characteristics of an eligible patient for the study, while exclusion criteria specify characteristics that render a patient ineligible for the clinical study. Inclusion and exclusion criteria can specify conditions, medications, lab results, family history, lifestyle practices, or any other clinical context represented in the universal graph.

In one implementation, the clinical research interface 100 can receive inclusion and exclusion criteria in natural language and, in real-time, convert these criteria to a clinical concept that represents a node in the target graph. In one example, the clinical concept is displayed to the user responsive to the natural language input. For example, if a user inputs text such as "patients with tachycardia and normal blood pressure" the clinical research interface 100 can display "[problem: tachycardia]; [vitals: systolic pressure<measure: 120 mmHg]; [vitals: systolic pressure>measure: 90 mmHg]; [vitals: diastolic pressure<measure: 80 mmHg]; [vitals: diastolic>measure: 60 mmHg]" indicating a node representing tachycardia categorized as a "problem" is now present in the target graph along with nodes for "systolic," "diastolic," "120 mmHg" etc. In this case, the "<" and ">" indications can represent edges indicating a less than or greater than relationship between "systolic" and "diastolic" nodes with the blood pressure "measure" nodes respectively. In one example, the clinical research interface 100 displays inclusion criteria and exclusion criteria at different locations or in different colors to indicate negation in the case of exclusion criteria.

In one implementation, the computer system can provide autocomplete functionality based on the ontologies in the universal graph. For example, if a user inputs a set of symptoms exhibited by a patient as a set of inclusion criteria, the computer system can utilize the universal graph to suggest a diagnosis that may result in the symptoms specified by the user. Alternatively or additionally, the computer system can receive a description of a diagnosis as an input from a user and suggest symptomatic criteria to the user. Furthermore, the computer system can utilize the universal graph to suggest synonymous or preferred terminology for an input received from a user. In one implementation, the computer system can render a pop-up or overlay proximate to a text input field in the clinical research interface 100 indicating the suggested related inclusion or exclusion criteria.

In one implementation, the clinical research interface displays a visual representation (e.g. a visualization of a "card" or an expanding organized list of possible criteria) of ontologies in the universal graph for selection by a user of the clinical research interface. The clinical research interface can categorize the visually represented ontologies based on the type of criteria and receive selection of particular criteria as inclusion or exclusion criteria (e.g. through a user clicking and dragging a visual representation of a criteria into an inclusion criteria region of the clinical research interface). For example, a UI element in the clinical research interface can represent "diagnoses" of a potential patient and, upon receiving an interaction from a user of the clinical research interface, associated with the UI element, the clinical research interface can reveal a categorized list of diagnoses a potential patient could have been given. The clinical research interface can then receive a selection, from the user, of diagnoses for inclusion or exclusion criteria. However, the clinical research interface can display ontologies of the universal graph for selection of inclusion and exclusion criteria in any other way.

5.2 Target Graph Generation

As shown in FIG. 1, in Block S140, the computer system transforms the first set of inclusion and exclusion criteria into a first target graph representing a first set of target clinical concepts for a clinical trial. Generally, the computer system transforms any inclusion and exclusion criteria recorded at the clinical research interface 100 into a target graph representing clinical concepts to be included or excluded in a clinical study. In one implementation, the computer system can transform the inclusion and exclusion criteria into a target graph as they are provided to the clinical research interface 100 in real-time.

In one variation, the computer system can ingest an electronic document of a clinical study proposal and, using the NLP and semantics engine, identify the inclusion and exclusion criteria of the clinical study automatically. Once the computer system identifies the inclusion and exclusion criteria of the clinical study, the computer system can display the identified inclusion and exclusion criteria to the user via the clinical research interface 100. In one example, the computer system can record changes to the identified inclusion and exclusion criteria made by the user via the clinical research interface 100.

5.3 Real-Time Potential Cohort Identification

As shown in FIG. 1 in Blocks S142 and S144, for each patient in the population of patients, in response to alignment between the patient graph of the patient and the first target graph, the computer system appends the patient to a first subpopulation of patients and renders a first representation of the first subpopulation of patients within the clinical research interface 100. Generally, the computer system performs a graph search or graph mining algorithm to determine matches between patient graphs and a target graph. In one implementation, the computer system solves a subgraph isomorphism problem between a universal graph and the target graph and then returns an index of patient graphs that are also isomorphic to the same subgraphs of the universal graph as the target graph. In another implementation, the computer system identifies patients with patient graphs that are morphologically similar to the target graph, as opposed to identifying only patients corresponding to isomorphic patient graphs.

The computer system renders an indication of the resulting matches via the clinical research interface 100. In one implementation, the computer system renders a visual indication of the number of matches accompanied by a scrollable list of matching patients at the clinical research interface 100. The computer system can also render a visual indication of the demographic composition of the matching patients in the form of a pie chart, histogram, or any other data visualization tool at the clinical research interface 100. The computer system can also render a map indicating the geographic distribution of matching patients.

In one implementation, the computer system can categorize or rank matching patients based on a similarity measure of a patient's corresponding patient graph to the target graph. Alternatively, the computer system can categorize the matching patients based on the particular differences between a patient's corresponding patient graph and the target graph. For example, if a target graph includes eight clinical concepts and a similar patient graph matches seven of the eight clinical concepts but is missing the clinical concept representing the patient having a healthy BMI, the computer system can render a graphic showing that the patient matches all clinical concepts but does not have a healthy BMI. Additionally or alternatively, the computer system can generate a list of patients satisfying various combinations of the clinical concepts represented in the target graph. The computer system can render an indication of the proportion of matching patients that are exact matches along with the proportion of patients that are missing a subset of the clinical concepts represented in the target graph, along with an identification (in natural language) of the missing clinical concept for each proportion of patients. Additionally, the computer system can differentially treat conflicting and absent criteria for each patient. Specifically, if a patient graph indicates an opposite or conflicting status in relation to an inclusion criterion or exactly matches an exclusion criterion the represented patient can be excluded from the results or can be otherwise designated as having evidence of a conflicting status. On the other hand, a patient graph that lacks evidence of a particular inclusion criterion or exclusion criterion could be designated as being potentially eligible or ineligible respectively. By categorizing the results in this way, the computer system provides users with information that may be useful in modifying the inclusion and exclusion criteria of a clinical study.

The computer system can render the results of the matching step in real-time, such that, if the clinical research interface 100 records a user input modifying any of the inclusion or exclusion criteria relied upon to generate the target graph, the computer system updates the clinical research interface 100 to reflect the changes to the results of the graph search in a minimally-perceptible period of time (e.g. less than 500 milliseconds).

The clinical research interface 100 can include an interactive graphical element that indicates completion of the patient search. In response to receiving an indication that the user has completed searching and is satisfied with a potential cohort, the computer system can render a list of patients in the potential cohort. The computer system can then record a selection of patients from the potential cohort and flag the selected patients for inclusion in the clinical study.

In one implementation, the computer system can also display a graphical indicator next to each patient name in the list showing the status of that patient in a potential clinical study. In one implementation, the computer system can indicate whether the patient in the potential clinical study: is eligible but not enrolled; is pending enrollment; is currently enrolled; is newly ineligible for the study; has declined an invitation to participate in the study; or has dis-enrolled from the study.

5.4 Cohort Analysis

The computer system can also further analyze the matching patient population in addition to rendering the results via the clinical research interface 100. In one implementation, the computer system can perform a sensitivity analysis for the inclusion and exclusion criteria of a patient search. The computer system can accomplish this by performing a series of patient searches modifying one inclusion or exclusion criterion at a time and recording the resulting change in the matching patient population (i.e. one-at-a-time sensitivity analysis). The computer system can then render the inclusion and exclusion criteria with accompanying visual indicators of the patient population's sensitivity to each criterion. For example, the computer system can color the visual representation of each inclusion or exclusion criterion, wherein a brighter color indicates greater sensitivity and a darker color indicates a lower sensitivity. Alternatively, the computer system can render a number indicating the change in population due to a potential removal of the criterion adjacent to the visual representation of the criterion.

In addition to performing sensitivity analyses, the computer system can also generate additional statistics for the matching patient population including averages or standard deviations of numerical characteristics of each patient, such as age, height, weight, BMI, etc. In one implementation, the computer system can leverage historical data to generate potential inclusion or exclusion criteria. The computer system can then render the potential criterion via the clinical research interface 100 for confirmation by a user.

5.5 System Feedback Via Supervised Learning

The computer system can also analyze inputs to the clinical research interface 100 to implement supervised learning and improve patient search results. The computer system can record successive inputs from a user at the clinical research interface 100 to the inclusion and exclusion criteria; if an input from a user changes a recently generated output of the computer system, the computer system can interpret this as a supervised input. For example, if a user inputs an inclusion criterion in natural language as "patients with a medical history including an ABG" and the computer system interprets the inclusion criterion as "[procedures: aortic bifurcation graft]," the user may correct this interpretation by removing the newly generated inclusion criterion and inputting: "[procedures: aortobifemural graft]." In this case, the user has effectively corrected the computer system's interpretation of "ABG." The computer system can record this event as a supervised event and incorporate into a supervised learning algorithm. As a result, the computer system may be more likely to choose the alternate interpretation of ABG in the future when provided the same context. In one implementation, if the computer system is unable to disambiguate a term with a threshold level of confidence, the computer system can prompt the user, via the clinical research interface 100, to clarify the term.

6. Point-of-Care Interface

As shown in FIG. 1 in Block S160, in response to access of a particular EHR of a particular patient included in the potential clinical cohort at a point-of-care interface 200, the computer system renders an indication of the particular patient's eligibility for the clinical trial. Generally, the point-of-care interface 200 can include an application operating on a device at the point-of-care of a health provider. For example, the point-of-care interface 200 can be displayed by a computer used by a doctor in an examination room, a mobile device used by a nurse to take notes, or any other device used by a clinician or other user in a clinical setting. The application displaying the point-of-care interface 200 (hereinafter "point-of-care application") can be associated with the computer system or can be a third-party application cooperating with the computer system. In some implementations, the point-of-care application can primarily serve as a portal to view patients that are eligible for clinical studies via the computer system, the point-of-care application's primary function is typically as EHR software for the provider. Thus, additional functions provided by the computer system can be seamlessly integrated into the EHR routine of providers.

6.1 Indications of Eligibility

As shown in FIG. 3, in one implementation, the point-of-care interface 200 includes an eligibility indicator, which includes a visual indicator that flashes, changes color, or otherwise alerts the user that a patient corresponding to a currently open EHR is eligible for at least one clinical study. For example, when a doctor opens the EHR of John Smith in the point-of-care application the eligibility indicator may indicate John Smith's eligibility for one or more clinical studies. If the point-of-care interface 200 records an interaction with the visual indicator, the point-of-care interface 200 can display additional information pertaining to the clinical study for which the patient is eligible. Additionally, the point-of-care interface 200 can display the clinical concepts associated with the patient that were identified as inclusion criteria in the clinical study for which the patient is eligible. Furthermore, the point-of-care interface 200 can display a graphical element, wherein upon recording an interaction on the graphical element from a user of the point-of-care application, the computer system can enroll the patient in the clinical study. For example, while viewing the EHR of John Smith, a doctor can select the eligibility indicator to review an option icon for enrolling in the clinical study. The doctor can then select the option icon to enroll John Smith in the clinical study.

However, the computer system can communicate patient eligibility for a clinical trial to a user at the point-of-care in any other way in Block S160.

6.2 Monitoring Eligibility

After a patient has been enrolled in a clinical study through the computer system, the computer system can continuously monitor the patient through the patient's EHR or through the point-of-care application. For example, the computer system can periodically generate a second patient graph for the patient and perform a second patient search using the target graph for the clinical study in which the patient has enrolled. If the second patient graph is not a match for the target graph of the clinical study, the patient is no longer eligible for the clinical study and can be removed from the clinical study. Alternatively, the computer system or the point-of-care application can monitor the patient's EHR for any changes and then regenerate the patient graph and perform a second patient search responsive to identifying a change in the EHR. The computer system can continue to reevaluate a patient's eligibility for a study in which the patient is enrolled until the end of the study.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for selecting a cohort for a clinical study, comprising:
    accessing from an electronic health record database, an unstructured electronic health record for each patient in a population of patients;
    for each patient in the population of patients:
        transforming the associated unstructured electronic health records of the patient into a patient graph, the patient graph representing a set of clinical concepts and corresponding semantic roles for the patient; and
        appending the patient graph to a set of patient graphs;
    at a clinical research interface, recording a first set of inclusion and exclusion criteria;
    transforming the first set of inclusion and exclusion criteria into a first target graph representing a first set of target clinical concepts for the clinical study;
    for each patient in the population of patients, in response to alignment between the patient graph of the patient and the first target graph, appending the patient to a first subpopulation of patients;
    rendering a first representation of the first subpopulation of patients within the clinical research interface;
    at the clinical research interface, recording a second set of inclusion and exclusion criteria;
    transforming the first set of inclusion and exclusion criteria and the second set of inclusion and exclusion criteria into a second target graph for the clinical study;
    for each patient in the population of patients, in response to alignment between the patient graph of the patient and the second target graph, appending the patient to a second subpopulation of patients;
    rendering a second representation of the second subpopulation of patients within the clinical research interface;
    recording a selection of a potential clinical cohort from the second subpopulation of patients;
    in response to access of a particular electronic health record of a particular patient included in the potential clinical cohort at a point-of-care interface, rendering a visual indicator of the particular patient's eligibility for the clinical study within the point-of-care interface;
    at the point-of-care interface, recording a first interaction with the visual indicator; and
    in response to recording the first interaction with the visual indicator, enrolling the particular patient in the clinical study,
    wherein the method further comprises:
        ingesting a corpus of medical data; and
        generating a universal graph based on the corpus of medical data;
    wherein transforming the associated unstructured electronic health records of the patient into the patient graph, comprises transforming the associated unstructured electronic health records of the patient into the patient graph based on the universal graph, the patient graph representing the set of clinical concepts and the corresponding semantic roles for the patient;
    wherein transforming the first set of inclusion and exclusion criteria into the first target graph comprises transforming the first set of inclusion and exclusion criteria into the first target graph, based on the universal graph, the first target graph representing the first set of target clinical concepts for the clinical study; and
    wherein transforming the first set of inclusion and exclusion criteria and the second set of inclusion and exclusion criteria into the second target graph for the clinical study comprises transforming the first set of inclusion and exclusion criteria and the second set of inclusion and exclusion criteria into the second target graph for the clinical study based on the universal graph.

2. The method of claim 1, wherein generating the universal graph based on the corpus of medical data comprises generating a set of context-specific universal graphs, each context-specific universal graph in the set of context-specific universal graphs representing a distinct clinical context.

3. The method of claim 1 further comprising:
for each patient in the population of patients, indexing the patient graph of the patient within the universal graph;
for each patient in the population of patients, detecting alignment between the first target graph and the patient graph of the patient by accessing a first index corresponding to the first target graph within the universal graph; and
for each patient in the population of patients, detecting alignment between the second target graph and the patient graph of the patient by accessing a second index corresponding to the second target graph.

4. The method of claim 3, wherein indexing the patient graph of the patient within the universal graph comprises:
identifying an isomorphic subgraph of the universal graph isomorphic with the patient graph; and
listing the patient of the patient graph in an index corresponding to the isomorphic subgraph.

5. The method of claim 3, wherein indexing the patient graph of the patient within the universal graph comprises:
identifying a set of morphologically similar subgraphs of the universal graphs morphologically similar to the patient graph; and
listing the patient of the patient graph in a set of indices corresponding to the set of morphologically similar subgraphs.

6. The method of claim 1, wherein recording the first set of inclusion and exclusion criteria comprises:
receiving a selection of a file representing the clinical study; and
extracting the first set of inclusion and exclusion criteria based on the file representing the clinical study.

7. The method of claim 1, for each inclusion criterion and exclusion criterion in the first set of inclusion and exclusion criteria and in the second set of inclusion and exclusion criteria:
generating a modified target graph without the criterion;
for each patient in the population of patients, in response to alignment between the patient graph of the patient and the modified target graph, appending the patient to a modified subpopulation of patients;
calculating a difference in population between the second subpopulation of patients and the modified subpopulation of patients; and
rendering a second visual indicator of the difference in population within the clinical research interface.

8. The method of claim 1, wherein rendering the visual indicator comprises rendering the visual indicator within a point-of-care application displaying an electronic health record of the particular patient.

9. The method of claim 1, wherein, in response to recording the interaction with the visual indicator, enrolling the particular patient in the clinical study comprises, in response to recording the interaction with the visual indicator:
rendering the first set of inclusion and exclusion criteria and the second set of inclusion and exclusion criteria applicable to the particular patient;
rendering an option icon for enrolling the particular patient in the clinical study; and
in response to recording an interaction with the option icon, enrolling the particular patient in the clinical study.

10. The method of claim 1, further comprising:
monitoring an unstructured electronic health record of the particular patient;
in response to detecting a change in the unstructured electronic health record of the patient, generating a second patient graph for the particular patient; and
in response to detecting that the second patient graph does not match the second target graph, removing the particular patient from the second subpopulation of patients.

* * * * *